US012377086B2

(12) United States Patent
Sham et al.

(10) Patent No.: US 12,377,086 B2
(45) Date of Patent: Aug. 5, 2025

(54) THERAPEUTIC METHODS, COMBINATIONS AND KITS

(71) Applicants: Yuk Yin Sham, Minneapolis, MN (US); Ramaiah Muthyala, Minneapolis, MN (US); Woo-Shik Shin, Minneapolis, MN (US)

(72) Inventors: Yuk Yin Sham, Minneapolis, MN (US); Ramaiah Muthyala, Minneapolis, MN (US); Woo-Shik Shin, Minneapolis, MN (US)

(73) Assignees: Yuk Yin Sham, Minneapolis, MN (US); Ramaiah Muthyala, Minneapolis, MN (US); Woo Shik Shin, Minneapolis, MN (US)

( * ) Notice: Subject to any disclaimer, the term of this patent is extended or adjusted under 35 U.S.C. 154(b) by 0 days.

(21) Appl. No.: 17/825,777

(22) Filed: May 26, 2022

(65) Prior Publication Data

US 2022/0401432 A1    Dec. 22, 2022

Related U.S. Application Data

(60) Provisional application No. 63/194,048, filed on May 27, 2021.

(51) Int. Cl.
| | | |
|---|---|---|
| A61K 31/43 | (2006.01) | |
| A61K 31/407 | (2006.01) | |
| A61K 31/424 | (2006.01) | |
| A61K 31/47 | (2006.01) | |
| A61P 31/04 | (2006.01) | |

(52) U.S. Cl.
CPC ............ *A61K 31/47* (2013.01); *A61K 31/407* (2013.01); *A61K 31/424* (2013.01); *A61K 31/43* (2013.01); *A61P 31/04* (2018.01)

(58) Field of Classification Search
CPC ........ A61K 31/47; A61K 31/424; A61P 31/04
See application file for complete search history.

(56) References Cited

U.S. PATENT DOCUMENTS 11,491,146 B2    11/2022    Sham et al.

FOREIGN PATENT DOCUMENTS

| WO | WO-2009140215 A2 * | 11/2009 | ............ A61K 31/47 |
| WO | 2013101600 A1 | 7/2013 | |

OTHER PUBLICATIONS

Abboud, M , et al., "Interaction of Avibactam with Class B Metallo-β-Lactamases", Antimicrobial Agents and Chemotherapy 60 (10), 5655-5662 (2016).
Blair, J , et al., "Molecular mechanisms of antibiotic resistance", Nat Rev Micro 13, 42-51 (2015).
(Continued)

*Primary Examiner* — Craig D Ricci
*Assistant Examiner* — Janet L Coppins
(74) *Attorney, Agent, or Firm* — Viksnins Harris Padys Malen LLP

(57) ABSTRACT

Therapeutic methods comprising the administration of 8-hydroxyquinoline-7-carboxylic acid or a pharmaceutically acceptable salt thereof and an antibacterial agent are disclosed. Also disclosed are combinations and kits comprising 8-hydroxyquinoline-7-carboxylic acid or a pharmaceutically acceptable salt thereof and an antibacterial agent.

1 Claim, 6 Drawing Sheets

(56) References Cited

OTHER PUBLICATIONS

Brem, J , et al., "Structural Basis of Metallo-B-Lactamase Inhibition by Captopril Stereoisomers", Antimicrob Agents Chemother 60, 142-150 (2016).

Bush, K , et al., "Updated Functional Classification of beta-Lactamases", Antimicrobial Agents and Chemotherapy 54(3), 969-976 (2010).

CDC , "Healthcare-associated Infections, Klebsiella pneumoniae in Healthcare Settings", Centers for Disease Control and Prevention, 3 pages (Nov. 24, 2010).

Chan, A , et al., "Role for dithiolopyrrolones in disrupting bacterial metal homeostasis", PNAS 114(10), 2717-2722 (2017).

Chen, P , et al., "2-Substituted 4,5-dihydrothiazole-4-carboxylic acids are novel inhibitors of metallo-β-lactamases", Bioorganic and Medicinal Chemistry Letters 22 (19), 6229-6232 (2012).

Chen, A , et al., "Dipicolinic Acid Derivatives as Inhibitors of New Delhi Metallo-β-lactamase-1", Journal of Medicinal Chemistry 60 (17), 7267-7283 (2017).

Chiem, K , et al., "Inhibition of Aminoglycoside 6'-N-Acetyltransferase Type Ib-Mediated Amikacin Resistance in Klebsiella pneumoniae by Zinc and Copper Pyrithione", Antimicrobial Agents and Chemotherapy 59(9), 5851-5853 (2015).

Das Gupta , et al., "Histone deacetylases in monocyte/macrophage development, activation and metabolism: refining HDAC targets for inflammatory and infectious diseases", Clin Transl Immunology 5(1), e62 (2016).

Drawz, S , et al., "New β-lactamase inhibitors: a therapeutic renaissance in an MDR world", Antimicrob Agents Chemother 58(4), 1835-1846 (2014).

Falconer, S , et al., "Zinc Chelation by a Small-Molecule Adjuvant Potentiates Meropenem activity in Vivo against NDM-1-Producing Klebsiella pneumoniae", ACS Infect Dis 1(11), 533-543 (2015).

Fujitani, S , et al., "Pneumonia Due to Pseudomonas aeruginosa Part I: Epidemiology, Clinical Diagnosis, and Source", Chest 139(4), 909-919 (2011).

Gonzalez-Bello, C , et al., "β-Lactamase Inhibitors To Restore the Efficacy of Antibiotics against Superbugs", Journal of Medicinal Chemistry 63 (5), 1859-1881 (2020).

Han, G , et al., "Study On the Active Principle of Polyalthia Nemoralis I . The Isolation and Identification of Natural Zinc Compound", Acta Chimica Sinica 39(5), 433-437 (1981). [English Abstract].

Hecker, S , et al., "Discovery of Cyclic Boronic Acid QPX7728, an Ultrabroad-Spectrum Inhibitor of Serine and Metallo-β-lactamases", Journal of Medicinal Chemistry 63 (14), 7491-7507 (2020).

Heinz, U , et al., "Coordination Geometries of Metal Ions in D- or L-Captopril-inhibited Metallo-β-lactamases", J Biol Chem 278, 20659-20666 (2003).

Jacobsen, F , et al., "The Design of Inhibitors for Medicinally Relevant Metalloproteins", J ChemMedchem 2, 152-171 (2007).

Kahraman, E , et al., "The Antibiotic Resistance Patterns of Klebsiella pneumoniae Clinic Isolates: A Comprehensive Meta-Analysis", Open Journal of Bacteriology, 021-026 (2017).

Krenn, B , et al., "Antiviral Activity of the Zinc Ionophores Pyrithione and Hinokitiol against Picornavirus Infections", J Virol 83, 58-64 (2009).

Marcheselli, M , et al., "Novel antifouling agent-zinc pyrithione: stress induction and genotoxicity to the marine mussel Mytilus galloprovincialis", Aquat Toxicol 102, 39-47 (2011).

Mombelli, M , et al., "Histone Deacetylase Inhibitors Impair Antibacterial Defenses of Macrophages", JID 204, 1367-1374 (2011).

Mulvey , et al., "New Delhi metallo-β-lactamase in Klebsiella pneumoniae and Escherichia coli, Canada", Emerg Infect Dis 17(1), 103-106 (2011).

Muthyala, R , et al., "Cell permeable vanX inhibitors as vancomycin re-sensitizing agents", Bioorganic & Medicinal Chemistry Letters 24, 2535-2538 (2014).

Muthyala, R , et al., "Discovery of 1-hydroxypyridine-2-thiones as selective histone deacetylase inhibitors and their potential application for treating leukemia", Bioorganic & Medicinal Chemistry Letters 25, 4320-4324 (2015).

Palzkill, T , "Metallo-β-lactamase structure and function", Ann N Y Acad Sci 1277, 91-104 (2013).

Qiu, M , et al., "Zinc ionophores pyrithione inhibits herpes simplex virus replication through interfering with proteasome function and NF-κB activation", Antivir Res 100, 44-53 (2013).

Rasheed, J , et al., "New Delhi Metallo-β-Lactamase-producing Enterobacteriaceae, United States", Emerg Infect Dis 19, 870-878 (2013).

Schwartz, J , et al., "Comparative evaluation of antidandruff clinical efficacy of a potentiated zinc pyrithlone shampoo and a zinc pyrithisone/climbazole combination formula", J Am Acad Dermatol 68(4), Supplment 1, p. AB46, P6172 (2013).

Shin, W , et al., "Discovery of 1-Hydroxypyridine-2(1H)-thione-6-carboxylic Acid as a First-in-Class Low-Cytotoxic Nanomolar Metallo β-Lactamase Inhibitor", ChemMedChem 12(11), 845-849 (2017).

Tailler, M , et al., "Antineoplastic activity of ouabain and pyrithione zinc in acute myeloid leukemia", Oncogene 31, 3536-3546 (2012).

Tehrani, K , et al., "Thiol-Containing Metallo-β-Lactamase Inhibitors Resensitize Resistant Gram-Negative Bacteria to Meropenem", ACS Infectious Diseases 3 (10), 711-717 (2017).

Tsivkovski, R , et al., "Biochemical Characterization of QPX7728, a New Ultrabroad-Spectrum Beta-Lactamase Inhibitor of Serine and Metallo-Beta-Lactamases", Antimicrobial Agents and Chemotherapy 64 (6), e00130-20 (2020).

Van Der Bij, A , et al., "First outbreak of VIIVI-2 metallo-f3-lacta111ase-producing Pseudomonas aeruginosa in The Netherlands: microbiology, epide111iology and clinical outomnes", International Journal of Antimicrobial Agents 37, 513-518 (2011).

Zhou, X , et al., "Stability and in vitro absorption of captopril, enalapril and lisinopril across the rat intestine", Biochem Pharmacol 47, 1121-1126 (1994).

Zhuang, C , et al., "Rapid Identification of Keap1-Nrf2 Small-Molecule Inhibitors through Structure-Based Virtual Screening and Hit-Based Substructure Search", J Med Chem 57, 1121-1126 (2014).

\* cited by examiner

Figures 3A, 3B, 3C, and 3D
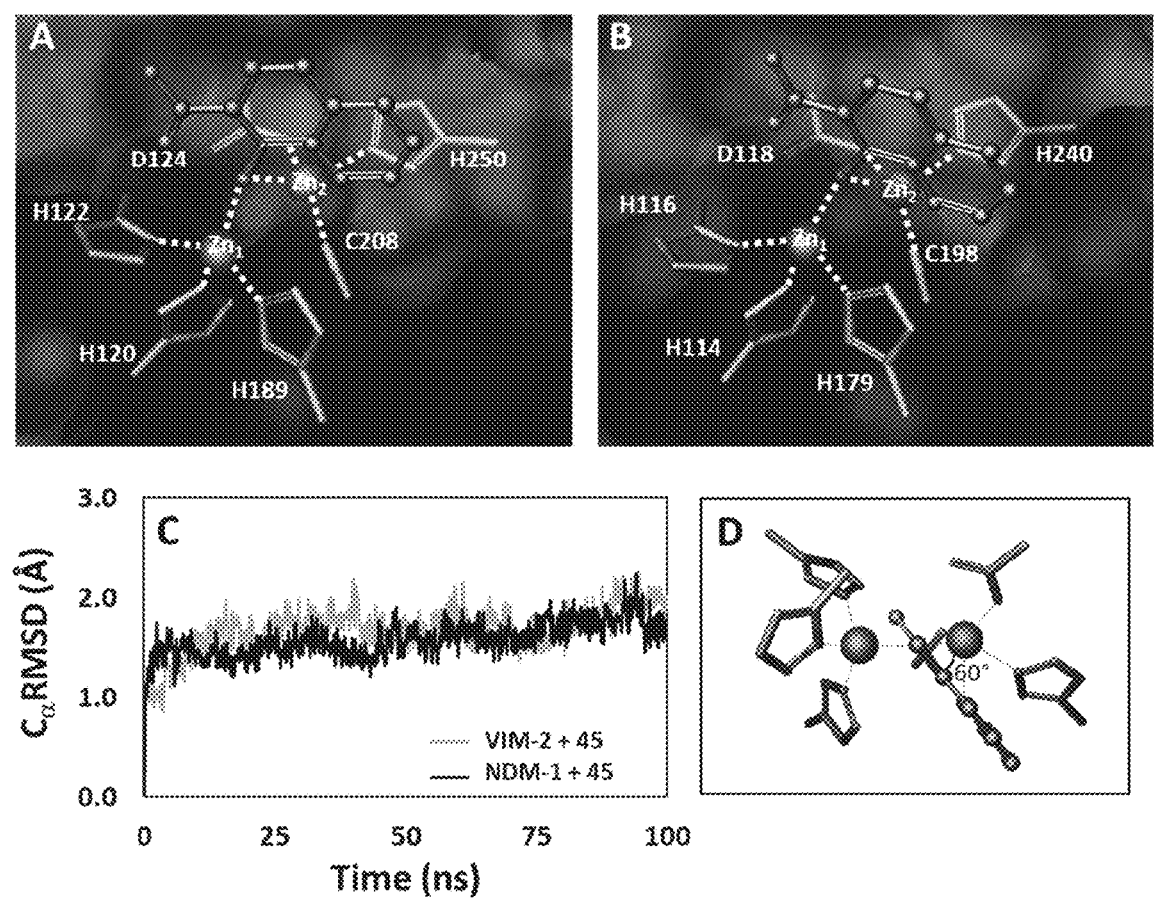

THERAPEUTIC METHODS, COMBINATIONS AND KITS

CROSS-REFERENCE APPLICATION

This application claims priority to U.S. Provisional Application No. 63/194,048 that was filed on May 27, 2021. The entire content of the application referenced above are hereby incorporated by reference herein.

BACKGROUND

β-Lactam antibiotics are the first line of defense against common bacterial infections. The expression of β-lactamases is one of the leading mechanism of multi-drug resistance in ESKAPE pathogens (Blair, J. M. A.; et al., Molecular mechanisms of antibiotic resistance. Nat Rev Micro 2015, 13, 42-51). The emergence of New Dehli metallo β-lactamase 1 (NDM-1) as a broad spectrum β-lactamase is a major public health concern in recent years (Rasheed, J. K.; et al., New Delhi metallo-beta-lactamase-producing Enterobacteriaceae, United States. Emerg Infect Dis 2013, 19, 870-8). Combination antibacterial therapy with β-lactamase inhibitors appears the only viable strategy for overcoming β-lactam drug resistance while maintaining the existing antibiotic arsenal. Given the variety of β-lactamases preexisting in nature, developing a broad spectrum β-lactamase inhibitor remains a challenge. There are currently three classes of FDA-approved β-lactamase inhibitors, consisting of β-lactams (sulbactam, tazobactam, and clavulanate), 1,6-diazabicyclo[3,2,1]octanes (avibactam, zidebactam, relebactam, nacubactam), and boron-based (vaborbactam) scaffolds, none of which demonstrates broad-spectrum activities against MBLs (Abboud et al., Antimicrobial Agents and Chemotherapy, 60 (10), 5655-5662, 2016; González-Bello et al., Journal of Medicinal Chemistry, 63 (5) 1859-1881, 2020; Hecker et al., Journal of Medicinal Chemistry, 63 (14) 7491-7507-18812020; Tsivkovski et al., Antimicrobial Agents and Chemotherapy, 64 (6), e00130-20, 2020). Other inhibitors such as 2,6-dipicolinic acid (Chen et al., Journal of Medicinal Chemistry, 60 (17), 7267-7283, 2017), thiazole-4-carboxylic acid (Chen et al., Bioorganic and Medicinal Chemistry Letters, 22 (19), 6229-6232, 2012), L-captopril (Brem et al., Antimicrobial Agents and Chemotherapy, 60 (1), 142-150, 2016), and thiol inhibitors (Tehrani & Martin, ACS Infectious Diseases, 3 (10), 711-717, 2017) have also been discovered but not useful. Only recently discovered boron-based inhibitor QPX7728 displays broad-spectrum activity and is currently in phase I clinical trials (Hecker et al., 2020; Tsivkovski et al., 2020). With the continuing emergence of nosocomial, β-lactam drug-resistant infections, there is an urgent and unmet need to discover novel classes of metallo-β-lactamase inhibitors (MBLi) for combination antibacterial therapy. To identify novel pharmacophores, we utilized VIM-2 and NDM-1, two carbapenemases commonly found in clinical isolates of ESKAPE pathogens, as the biochemical screening platform for MBLi discovery.

Fragment based screening (FS) with a metal chelator library is a powerful tool for the identification of a lead pharmacophore for zinc binding. Such screening allows for the direct comparison among potential pharmacophores of their inhibitory potency prior to their selection as the lead compound. There are risks associated with such an approach, including the possibility that the most potent chelating group may be too potent and non-selective in off-target inhibition and can thus result in unwanted cytotoxicity. However, given the variety of metallo β-lactamases (MBLs) to be targeted, such an approach may expedite the discovery of a broad spectrum MBLi with a pharmacophore with inherently high ligand efficiency.

Hit-based substructure search (HBSS) is a powerful strategy for developing early structural activity relationship (SAR) for drug discovery after initial screenings. As commercially available chemical libraries are innately enriched with synthesizable analogues, HBSS based on the scaffold of the hit compound can identify other related compounds to provide informative SAR. This approach commonly referred to as SAR by catalog, is both economical and highly efficient to achieve preliminary SAR for large numbers of chemically diverse hits prior to medicinal chemistry exploration. A recent report has successfully demonstrated this strategy with structure-based virtual screening in the identification of novel classes of protein-protein interaction inhibitors against Keap1-Nrf2 (C. L. Zhuang, et al., Rapid Identification of Keap1-Nrf2 Small-Molecule Inhibitors through Structure-Based Virtual Screening and Hit-Based Substructure Search, J Med Chem, 57 (2014) 1121-1126). Thus, as described herein, a combined strategy involving fragment based screening (FS) with a representative metal chelator library was utilized to study metallo β-lactamases.

There is currently a need for new methods to treat bacterial infections including methods utilizing new β-lactamase inhibitors (e.g., metallo β-lactamase inhibitors). There is also a need for new methods that utilize β-lactamase inhibitors (e.g., metallo β-lactamase inhibitors) with better properties such as lower toxicity, fewer off-target interactions or improved metabolic stability.

SUMMARY OF INVENTION

One embodiment provides a method for treating or preventing a bacterial infection in an animal (e.g., a mammal such as a human) comprising administering to the animal (a) 8-hydroxyquinoline-7-carboxylic acid or a pharmaceutically acceptable salt thereof, and (b) at least one antibacterial agent or a pharmaceutically acceptable salt thereof.

One embodiment provides a method for treating or preventing a bacterial infection in an animal (e.g., a mammal such as a human) comprising administering to the animal (a) a compound disclosed herein or a pharmaceutically acceptable salt thereof (e.g., a compound selected from compound 1-50 or a pharmaceutically acceptable salt thereof, compound 31-50 or a pharmaceutically acceptable thereof, compound 39-50 or a pharmaceutically acceptable salt thereof, and compound 41-50 or a pharmaceutically acceptable thereof, and (b) at least one antibacterial agent or a pharmaceutically acceptable salt thereof.

One embodiment provides a combination of (a) 8-hydroxyquinoline-7-carboxylic acid or a pharmaceutically acceptable salt thereof, and (b) an antibacterial agent or a pharmaceutically acceptable salt thereof.

One embodiment provides a kit comprising (a) 8-hydroxyquinoline-7-carboxylic acid or a pharmaceutically acceptable salt thereof, (b) an antibacterial agent or a pharmaceutically acceptable salt thereof (c) a container, and (d) a package insert or label indicating the administration of (a) and (b).

One embodiment provides a combination of (a) 8-hydroxyquinoline-7-carboxylic acid or a pharmaceutically acceptable salt thereof, and (b) an antibacterial agent or a pharmaceutically acceptable salt thereof for the prophylactic or therapeutic treatment of a bacterial infection.

One embodiment provides the use of (a) 8-hydroxyquinoline-7-carboxylic acid or a pharmaceutically acceptable salt thereof, and (b) an antibacterial agent or a pharmaceutically acceptable salt thereof for the preparation of a medicament for the prophylactic or therapeutic treatment of a bacterial infection in an animal (e.g., a mammal such as a human).

One embodiment provides a kit comprising (a) 8-hydroxyquinoline-7-carboxylic acid or a pharmaceutically acceptable salt thereof, (b) an antibacterial agent or a pharmaceutically acceptable salt thereof (c) a container, and (d) a package insert or label indicating the administration of (a) and (b) for the prophylactic or therapeutic treatment of a bacterial infection in an animal (e.g., a mammal such as a human).

BRIEF DESCRIPTION OF FIGURES

FIGS. 3A and 3B illustrate the modeled mode of binding 8-hydroxyquinoline-7-carboxylic acid within the binding site of; FIG. 3A VIM-2, FIG. 3B NDM-1.

FIG. 3C illustrates the $C_\alpha$RMSD analysis of bound VIM-2 and NDM-1 in complex with 45.

FIG. 3D illustrates the top view of 45 within the NDM-1 active site.

DETAILED DESCRIPTION

Figure 1A:
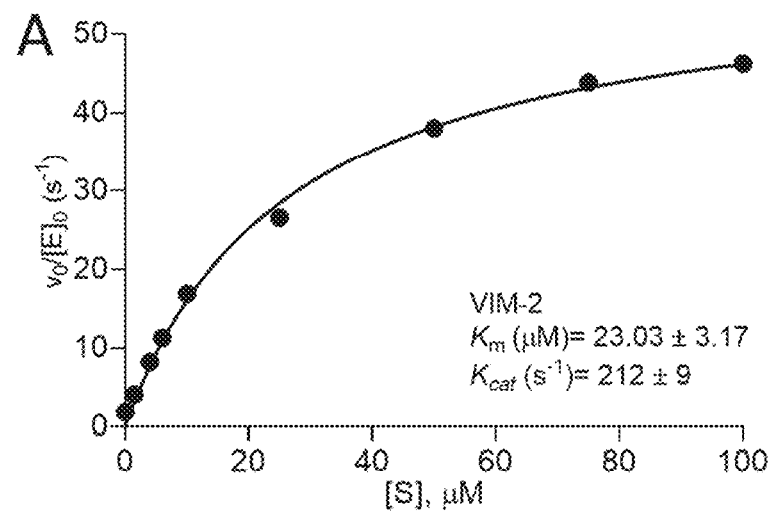
FIG. 1A illustrates the Steady-state kinetics for the hydrolysis of nitrocefin by VIM-2.

The following definitions are used, unless otherwise described.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to the lessening of an undesired physiological change or disorder, such as, for example, the development or spread of a bacterial infection. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. Thus the term treat as described above does not include prevention.

The term "patient" as used herein refers to any animal including mammals such as humans, higher non-human primates, rodents, domestic and farm animals such as cows, horses, pigs, sheep, dogs and cats. In one embodiment, the patient is a human patient. In one embodiment, the mammal is a human. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "package insert" is used to refer to instructions customarily included in commercial packages of therapeutic products, that contain information about the indications, usage, dosage, administration, contraindications and/or warnings concerning the use of such therapeutic products.

Antibacterial Agents

Antibacterial agents useful in the methods, combinations, and uses described herein include β-lactam antibiotics or a pharmaceutically acceptable salts thereof. Such antibacterial agents include but are not limited to Amoxcillin, Imipenem, Ampicillin, Ceftazidime, Piperacillin, Cefepime, Cefozopran, Cefpirome, Cefquinome, Ceftaroline fosamil, Ceftolozane, Ceftobiprole, Ceftiofur, Cefquinome, and Cefovecin. Additional antibacterial agents can also be useful in the methods, combinations, and uses described herein. Such antibacterial agents include but are not limited to glycopeptides, aminoglycoside, fluoroquinolones, polymyxins, rifamycins, lipiarmycins, quinolones, sulfonamides, macrolides, lincosamides, tetracyclines, cyclic lipopeptides, glycylcyclines, and lipiarmycins.

β-Lactamase Inhibitors and Serine β-Lactamase Inhibitors

The inclusion of one or more additional β-lactamase inhibitors may also be useful in the methods, combinations, kits and uses described herein. Such β-lactamase inhibitors include but are not limited to Sulbactam, Tazobactam, Clavulanic acid, and Avibactam. The inclusion of one or more serine β-lactamase inhibitors may also be useful in the methods, combinations, kits and uses described herein.

Treatment or Prevention of Bacterial Infections

The treatment or prevention of bacterial infections as described herein include but are not limited to infections that are caused by pathogens that express or overexpress a metallo β-lactamase. Such pathogens include ESKAPE pathogens. ESKAPE pathogens include *Enterococcus faecium, Staphylococcus aureus, Klebsiella pneumoniae, Acinetobacter baumannii, Pseudomonas aeruginosa,* and *Enterobacter* species.

Specific embodiments listed below are for illustration only; they do not exclude other defined embodiments or values or other values within defined ranges. It is to be understood that two or more embodiments may be combined.

In one embodiment 8-hydroxyquinoline-7-carboxylic acid or a salt thereof is an inhibitor of β-lactamase.

In one embodiment the β-lactamase is a metallo β-lactamase.

In one embodiment the metallo β-lactamase is VIM-2 or NDM-1.

In one embodiment the antibacterial agent or a pharmaceutically acceptable salt thereof is a β-lactam antibiotic or a pharmaceutically acceptable salt thereof.

In one embodiment the antibacterial agent or a pharmaceutically acceptable salt thereof is Amoxcillin, Imipenem, Ampicillin, Ceftazidime, Piperacillin, Cefepime, Cefozopran, Cefpirome, Cefquinome, Ceftaroline fosamil, Ceftolozan, Ceftobiprole, Ceftiofur, Cefquinome or Cefovecin.

In one embodiment the antibacterial agent or a pharmaceutically acceptable salt thereof is Amoxcillin, Imipenem, Ampicillin, Ceftazidime, Piperacillin, Cefepime, Cefozopran, Cefpirome, Cefquinome, Ceftaroline fosamil, Ceftolozan, or Ceftobiprol.

In one embodiment the antibacterial agent or a pharmaceutically acceptable salt thereof is Ceftiofur, Cefquinome, or Cefovecin.

In one embodiment the antibacterial agent comprises a combination of two or more antibacterial agents.

In one embodiment the antibacterial agent comprises a combination of two or more antibacterial agents wherein the combination is selected from the group consisting of (a) Amoxicillin and clavulanic acid or salts thereof, (b) Imipenem and cilastatin or salts thereof, (c) Ampicillin and flucloxacillin or salts thereof, (d) Ampicillin and sulbactam or salts thereof, (e) Ceftazidime and avibactam or salts thereof, (f) Piperacillin and tazobactam or salts thereof, and (g) Ceftolozane and tazobactam or salts thereof.

In one embodiment the bacterial infection is a drug resistant bacterial infection.

In one embodiment the bacterial infection is a multi-drug resistant bacterial infection.

In one embodiment the bacterial infection is caused by a pathogen that is resistant to a β-lactam antibiotic.

In one embodiment the bacterial infection is caused by a pathogen which expresses a metallo β-lactamase.

In one embodiment the bacterial infection is caused by a pathogen which overexpresses a metallo β-lactamase.

In one embodiment the metallo β-lactamase is a B1 metallo β-lactamase.

In one embodiment the metallo β-lactamase is IMP, VIM, or NDM.

In one embodiment the metallo β-lactamase is VIM-2 or NDM-1.

In one embodiment the bacterial infection is caused by a pathogen comprising one or more plasmids selected from NDM, SMB, EBR, SFB, BcII, CcrA, BalB, IND, EBR, SFB, SFH, IMP, VIM, SPM, GIM, DIM, SIM, CphA, ImiS, Sfh, L1, GOB, FEZ, THIN-B, Mbl1b, CAU, and BJP type genes.

In one embodiment the bacterial infection is caused by one or more ESKAPE pathogens (*Enterococcus faecium, Staphylococcus aureus, Klebsiella pneumoniae, Acinetobacter baumannii, Pseudomonas aeruginosa,* or *Enterobacter* species).

In one embodiment the bacterial infection is caused by *Enterococcus faecium* (including VRE), *Staphylococcus aureus* (including MRSA, MSSA), *Klebsiella pneumoniae, Acinetobacter baumannii, Pseudomonas aeruginosa, Enterobacter* species (including ESBL), *Escherichia coli, Neisseria Gonorrhoeae, Campylobacter, Clostridium difficile, Salmonella, Salmonella* serotype *Typhi, Shigella, Streptococcus pneumoniae,* or *Mycobacterium tuberculosis*.

In one embodiment the animal is a mammal.
In one embodiment the animal is a human.
In one embodiment the animal is a non-human animal.
In one embodiment the animal is a non-human mammal.
In one embodiment the administration is separate.
In one embodiment the administration is sequential.
In one embodiment the administration is simultaneous.

In cases where compounds described herein are sufficiently basic or acidic, a salt of the compound can be useful as an intermediate for isolating or purifying a compound described herein.

Additionally, administration of a compound described herein as a pharmaceutically acceptable acid or base salt may be appropriate. As used herein, the term "pharmaceutically acceptable salts" is meant to include salts of the active compounds which are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The compounds described herein can be formulated as pharmaceutical compositions and administered to a mammalian host, such as a human patient in a variety of forms adapted to the chosen route of administration, i.e., orally or parenterally, by intravenous, intramuscular, topical or subcutaneous routes. In one embodiment the compounds described herein can be administered to the mammal (e.g., human patient) as a prodrug of the compound.

Thus, the compounds described herein may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds described herein may be applied in pure form, i.e., when they are liquids. However, the compounds described can also be administered to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds described herein to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949. The amount of the compounds, or an active salts or derivatives thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compounds described herein can be conveniently formulated in unit dosage form; for example, containing 5 to 1000 mg, or 10 to 750 mg, or 50 to 500 mg of active ingredient per unit dosage form. In one embodiment, the invention provides a composition comprising a compound described herein formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, one or more of the compounds described herein are co-administered. Co-administration of the compounds described herein (optionally with one or more other active therapeutic agents) generally refers to simultaneous or sequential administration of a compound described herein. In one embodiment therapeutically effective amounts of the compounds co-administered are present in the body of the patient.

In some embodiments, one or more of the compounds disclosed herein are co-administered by combining the compounds disclosed herein in a unitary dosage form for simultaneous or sequential administration to a patient. Thus, this combination therapy may be administered as a simultaneous or sequential regimen. When administered sequentially, the combination may be administered in two or more administrations.

The invention will now be illustrated by the following non-limiting Examples.

Example 1

Materials and Methods

Materials

All screening compounds were hand-selected from our in-house chemical library previously purchased commercially at 97% purity and above grade from Sigma Aldrich InterBioScreen, or from Combi-Blocks. 10 mM stock concentration of each compound were prepared in 2% DMSO.
Protein Expression and Purification For the biochemical assay, the bla$_{VIM2}$ gene, from a clinical strain of *P. aeruginosa*, was expressed using the pET24a (+) vector (L. Borgianni, et al., Mutational Analysis of VIM-2 Reveals an Essential Determinant for Metallo-beta-Lactamase Stability and Folding, Antimicrob Agents Ch, 54 (2010) 3197-3204). The pET24a-VIM-2 plasmid was transformed into competent BL21 (DE3) *E. coli* cells. The cells were plated onto an LB-agar plate with kanamycin (25 μg/mL) and incubated overnight at 37° C. A single colony was used to inoculate 50 mL of LB, containing 25 μg/mL kanamycin, and the culture was shaken overnight at 37° C. From the overnight culture, 10 mL were transferred to 4×IL LB medium containing 25 μg/mL kanamycin. The cultures were grown at 37° C. until an optical density (OD$_{600\ nm}$) of 0.6-0.8 was reached, at which point protein production was induced with IPTG (0.5 mM) and ZnCl$_2$ (100 μM). The temperature was reduced to 20° C., and the cells were shaken for an additional 18 h. The cultures were harvested by centrifugation (8 Kxg) for 10 min at 4° C. The resulting pellets were re-suspended in 25 mL of 50 mM HEPES, pH 7.5, containing 500 mM NaCl (buffer B). The cells were lysed with three passes through a French Press. The lysate was centrifuged (15 Kxg) for 30 min at 4° C. The supernatant was dialyzed against 2 L of 50 mM HEPES, pH 7.5 (buffer A), for 4 h. Buffer A was used to equilibrate a 25 mL Q-Sepharose column using an FPLC. The sample was loaded onto the column, and proteins were eluted with a linear gradient 0-500 mM NaCl with buffer B. Fractions containing VIM-2, determined by SDS-PAGE, were pooled and concentrated to 2-3 mL in an Amicon ultraconcentrator equipped YM-10 membrane. Further purification was conducted with a Sephacryl S-200 gel filtration column using 50 mM HEPES, pH 7.5, containing 150 mM NaCl. Fractions containing pure VIM-2 were pooled, and metal analysis was performed.

NDM-1 was expressed and purified as previously described with some adjustments (Yang, H.; et al., Spectroscopic and Mechanistic Studies of Heterodimetallic Forms of Metallo-beta-lactamase NDM-1. Journal of the American Chemical Society 2014, 136, 7273-7285). BL21 (DE3) *E. coli* cells containing the pET26b-ndm-1 plasmid were used to inoculate a 50 mL LB starter culture containing kanamycin (25 μg/mL). The culture was grown overnight at 37° C. The starter culture was then used to inoculate 4×1 L LB containing kanamycin (25 μg/mL). These flasks were incubated at 37° C. until culture reached an optical density of (OD$_{600}$) of 0.6 to 0.8. The incubator was then set to 22° C. and the cultures were shaken for 30 min to allow them to cool. ZnCl$_2$ (100 M) and IPTG (0.5 mM) were then added to the cultures and they were grown for 18 h at 22° C. The cells were then harvested using centrifugation (8000×g) for 10 min. The pellet was resuspended with 25 mL 50 mM HEPES, pH 7.5 containing 500 mM NaCl (Buffer B). Lysis was performed with three passes through a French Press. The lysate was centrifuged for 30 min (15,000×g) at 4° C. The supernatant was then dialyzed versus 2 L 50 mM HEPES, pH 7.5 (Buffer C) for 4 h. An FPLC was used to equilibrate a Q-Sepharose column using buffer C using a flowrate of 2.0 mL/min for 1.5 h. The lysate was then loaded onto the column and eluted with a linear NaCl gradient from 0-500 mM. Fractions containing NDM-1 were identified with SDS-PAGE. These fractions were pooled and concentrated to 2-3 mL in an Amicon ultracentrifugation concentrating unit with a YM-10 membrane. The resulting protein mixture was then loaded onto a Sephacryl S-200 gel filtration column run with 50 mM HEPES, pH 7.5 containing 150 mM NaCl (Buffer A). SDS-PAGE was used to identify fractions containing pure protein.
Biochemical Assay Nitrocefin (Cayman, CAS 41906-86-9) was used as the chromogenic substrate for all biochemical assays. The enzymatic activity of purified VIM-2 and NDM-1 were determined spectrophotometrically (spectramax-M5-reader) at room temperature in 50 mM potassium phosphate buffer at pH 7.0. The rate of product formation was monitored based on the $\lambda_{max}$=486 nm absorbance taken at 10 s intervals for 30 mins. The $K_m$ and $k_{cat}$ values were determined from 10 different concentrations of nitrocefin ranging from 0.001 to 100 μM with at least four independent initial-velocity measurements. Velocity versus substrate concentration curves were fitted by nonlinear regression using Michaelis-Menten Enzyme kinetics with Graphpad Prism 6.
Single Dose Enzymatic Inhibition Assay To identify potential MBL inhibitors, the relative change in the formation of hydrolyzed nitrocefin between treated and untreated MBL was determined as percentage inhibition. 5 nM of each BML was pre-incubated for 10 mins with 50 μM of each compound, followed by the addition of 10 μM nitrocefin. The relative change in the $\lambda_{max}$=486 nm absorbance after 30 mins was evaluated as percentage inhibition.
Dose Response Enzymatic Inhibition Assay and Inhibition Constant Each inhibitor was pre-incubated at concentrations from 0.001 to 50 μM with 5 nM each BML for 5 mins at room temperature in PBS buffer at pH 7.0 before addition of 10 μM nitrocefin. The rate of product formation was monitored based on the $\lambda_{max}$=486 nm absorbance taken at 10 s intervals for 30 mins. The relative change in absorbance was evaluated as percentage inhibition and the IC$_{50}$ was determined by fitting the data to a sigmoidal dose-response curve. The enzyme inhibition constant ($K_i$) was derived from initial-velocity measurements by nonlinear regression using competitive-inhibition enzyme kinetics using Graphpad Prism 6.

Equilibrium Dialysis

VIM-2 was diluted to 6 µM with 50 mM HEPES, pH 7.5, containing 150 mM NaCl. The diluted protein solution was used to make several 5 mL aliquots. L-Captopril, EDTA, 31, 41, and 43 were each added to two aliquots. One aliquot contained one molar equivalent of inhibitor (6 µM), with respect to enzyme concentration, and the second aliquot contained two molar equivalents (12 µM). One aliquot contained no inhibitor. Each aliquot was then incubated for 4 h at 4° C. Following incubation, each aliquot was dialyzed versus 500 mL of 50 mM HEPES, pH 7.5, for 4 h at 4° C. The aliquots were analyzed using ICP-AES, as previously described REF. The emission wavelengths used were 213.856, 238.892, 259.940, 231.604, and 324.754 nm for Zn, Co, Fe, Ni, and Cu, respectively.

Bacteria Cell Culture

Both *Escherichia coli* BL21 (DE3) cells (Invitrogen) and its transformed cell lines with plasmid pet24a-VIM-2 have been reported previously (M. F. Mojica, et al., Exploring the Role of Residue 228 in Substrate and Inhibitor Recognition by VIM Metallo-beta-lactamases, Biochemistry-Us, 54 (2015) 3183-3196). The optical density of the cell cultured was monitored at 600 nm ($OD_{600\ nm}$). The cells were cultured on 0.8 g/100 ml nutrient agar plate at pH 7.0 and 37° C. The bacterial growth medium was diluted in nutrient broth (NB) to a concentration absorbance of 1.5 and incubated overnight in 10 ml capped culture tubes with shaking. An overnight culture of the bacterial strain was sub-cultured to 0.06 $OD_{600\ nm}$ into the NB medium and was then seeded at max 200 µl into the wells of a 96 well microtiter plate. Samples were then incubated at 37° C. and shaken at 200 rpm for 18 h. The absorbance was measured on an ELIZA plate reader and analyzed with the Gen5™ software suite (version 1.08).

Half Maximal Effective Concentration ($EC_{50}$)

The bacterial culture was prepared as described above. The diluted subculture bacteria in NB medium were set up to a final volume of 200 µl in clear flat-bottom 96-well plates containing ten different concentrations of each tested compound ranging from 0.001 µM to 50 µM. The mixing of the bacterial culture plate were then incubated in a 37° C. stationary shaken incubator at 200 rpm for 18 h before measuring their optical density at 600 nm. The $EC_{50}$ were obtained by fitting the data to a sigmoidal dose-response equation using Graphpad Prism 6.

Human Cell Line Culture

Human embryonic kidney cell line (HEK293) were grown in 100 mm cell culture petri dishes at 37° C. with 5% $CO_2$ in Dulbecco's Modified Eagle's Medium high glucose medium containing 1% penicillin/streptomycin (Sigma-Aldrich, St. Louis, MO) and supplemented with 5% of fetal bovine serum (Thermo Fisher Scientific Gibco®). Cells under 10 passages and the 80% of monitored cell petri dish were used for experiment.

Human Cell Cytotoxicity Assays

Cytotoxicity of tested compounds were estimated using the MTT method. Cell viability were measured by counting viable cells by using the 3 (4,5dimethylthiazol-2-yl)-2,5-diphenyltetrazolium bromide (MTT) (Sigma-Aldrich, St. Louis, MO) colorimetric dye-reduction assay. The monolayer was trypsinized from cell culture Petri dishes and the cells were seeded in 96-well plates at the density of $5 \times 10^4$ cells/well (200 µl/well) in a culture medium containing 5% FBS. Following 24 h incubation and attachment, the cells were incubated for 72 h with different concentrations of inhibitors (0.01~100 µM) in culture media without FBS. The Control cells were supplemented only with a medium without containing FBS. All samples in 96 well plate were incubated at 37° C. at an atmosphere of 5% $CO_2$. After 72 hrs, 15 µl of MTT (5 mg/ml) dye was added to each well and the plates were incubated for 4 hours at 37° C. in 5% $CO_2$ incubator. After centrifuge with 1,500 rpm/15 mins, the supernatant was removed from each wells and 200 µl of dimethyl sulfoxide (DMSO) per well were added and the plates were gently shaken to solubilize the formed formazan for 30 min. The absorbance was measured using a microplate reader at wavelength 590 nm. The $CC_{50}$ were obtained based on a comparison with untreated cells by fitting the data to a sigmoidal dose-response equation using Graphpad Prism 6.

Molecular Modeling

All modeling was performed using the Schrodinger modeling package (Schrodinger LLC, N. Y., NY. Maestro v9.7, Bioluminate v1.2, Canvas v1.9, Epik v2.7, Glide v6.2, LigPrep v2.9, MacromModel v10.3, Prime v3.5, Schrodinger LLC, New York, NY, 2014). The modeling study was based on the X-ray crystallographic structures of VIM-2 (PDB: 4NQ2) (Aitha, M.; et al., Biochemical, Mechanistic, and Spectroscopic Characterization of Metallo-beta-lactamase VIM-2. *Biochemistry—Us* 2014, 53 (46), 7321-7331) and NDM-1 ((PDB: 4EXS) (King, D. T.; et al., New Delhi Metallo-β-Lactamase: Structural Insights into β-Lactam Recognition and Inhibition. 2012). All missing sidechains and hydrogen atoms were added with standard protein preparation protocols at physiological pH, followed by energy minimization using OPLS-AA 2005 force field with implicit solvent to optimize all hydrogen-bonding networks. Modeling of the bound state was based on the observed mode of 8HQ binding from *Aeromonas proteolytica* aminopeptidase (PDB: 3VH9) (Hanaya, K., et al., Potent inhibition of dinuclear zinc (II) peptidase, an aminopeptidase from *Aeromonas proteolytica*, by 8-quinolinol derivatives: inhibitor design based on Zn2+ fluorophores, kinetic, and X-ray crystallographic study. *JBIC Journal of Biological Inorganic Chemistry* 2012, 17 (4), 517-529) via superpositioning of the dinuclear zinc.

Molecular Dynamics

Molecular dynamics (MD) simulations were carried out using Desmond (E. Shaw Research, N. Y., NY *Desmond Molecular Dynamics System*, 2018.1; 2018). Each modeled complexes were solvated with a 15 Å buffer region from its outer edge inside an orthorhombic box of TIP3P explicit solvent model (Jorgensen, W. L.; et al., Comparison of simple potential functions for simulating liquid water. *J. Chem. Phys* 1983, 79, 926-935). 0.15 M $Na^+$ and $Cl^-$ counter ions were added to electroneutralize the final system. Each MD simulation was performed using Desmond with default protocol for initialization, followed by 100 ns unrestrained production simulation run under isothermal isobaric (NPT) conditions at 310 K and 1 atm with the OPLS3 force field. The stability of the protein complexes was assessed by evaluating the protein $C_\alpha$ root-mean-square-deviation ($C_\alpha$RMSD) with respect to the minimized starting structure.

Human Plasma Stability Study

The plasma stability assay was performed in triplicate by incubating the test compound in normal human plasma at 37° C. At 0, 1, 3, 6, and 24 h, aliquots of the plasma mixture were taken and quenched with 3 volumes of acetonitrile. The samples were then vortexed and centrifuged at 14,000 rpm for 3 min at 4° C. The supernatants were collected and analyzed by LC-MS/MS to determine the remaining percentage at various time points and to calculate plasma half-life ($t_{1/2}$).

Human Microsomal Stability Study

The in vitro microsomal stability assay was conducted in triplicate in human liver microsomal systems. In a typical incubation, the test compound was spiked into the reaction mixture containing 0.5 mg/mL of liver microsomal protein and 1 mM of NADPH in 0.1 M potassium phosphate buffer (pH 7.4) at 37° C. At various time points, 1 volume of reaction aliquot was taken and quenched with 3 volumes of acetonitrile. The samples were then vortexed and centrifuged at 14,000 rpm for 3 min at 4° C. The supernatants were collected and analyzed by LC-MS/MS to determine the in vitro metabolic half-life ($t_{1/2}$) and intrinsic clearance ($CL_{int}$).

Results and Discussion

As the focus is to target MBLs, the chemical diversity available for zinc chelators is expected to be significantly smaller than traditional fragment-based screening libraries. Furthermore, the power of HBSS relies on screening only fragments from commercial libraries with already enriched analogs for follow up SAR by catalog study. A fragment library of 31 small molecular chelators (InterBioScreen) was evaluated at single dose concentration against VIM-2 and NDM-1 (Table 1). This commercially acquired fragment library consisted of compounds with molecular weight ranging from 120 to 250 and metal chelating groups such as thiols, mercaptocarboxylic acids, hydroxamic acids, picolinic acids, and 8-hydroxyquinoline (8HQ). L-captopril, 1, a potent inhibitor for both VIM-2 and NDM-1, and SAHA, 15, a zinc binding HDAC inhibitor for the treatment of cutaneous T cell lymphoma, were also included as controls.

Overall, NDM-1 was more susceptible to inhibition than VIM-2. Of the 31 compounds evaluated, 14 compounds exhibited more than 50% inhibition against NDM-1. 8-Hydroxyquinoline (8HQ), 31, was the most active, exhibiting over 96% inhibition against both NDM-1 and VIM-2, comparable to that of L-captopril, 1. Compounds 20, 21 (derivatives of pthalazines), 24, 25, and 29 (picolinic acids) exhibit more than 50% inhibitory activity and up to 87% against NDM-1 than VIM-2. Other compounds 5, 13, and 17 showed only modest broad-spectrum inhibition activity at 40% against both MBLs. Overall, the initial single dose screening data of the fragment library identified 8-hydroxyquinoline (8HQ, 31) as a promising broad-spectrum MBLi (Chen, A. L. Y.; et al., Dipicolinic Acid Derivatives as Inhibitors of New Delhi Metallo-beta-lactamase-1. *J Med Chem* 2017, 60 (17), 7267-7283).

TABLE 1

| Compound | Compound | VIM-2 | NDM-1 |
|---|---|---|---|
| 1 | [structure: L-captopril] | 97 | 93 |
| 2 | [structure: ethyl 2-mercaptoacetate] | 16 | 55 |
| 3 | [structure: 2-mercaptopropanoic acid] | 17 | 50 |
| 4 | [structure: 2-mercaptosuccinic acid] | 22 | 39 |
| 5 | [structure: pyridyl mercaptoacrylic acid] | 40 | 39 |
| 6 | [structure: 2-mercapto-4-hydroxypyrimidine] | 13 | 48 |

TABLE 1-continued
| | 50 uM single dose percentage inhibition assay | | |
|---|---|---|---|
| Compound | Compound | VIM-2 | NDM-1 |
| 7 | 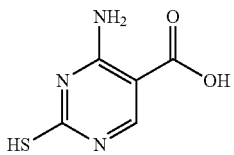 [SMILES: Nc1nc(S)ncc1C(=O)O] | 9 | 44 |
| 8 | 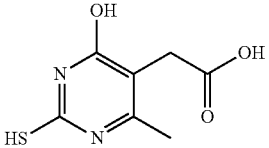 | 18 | 63 |
| 9 | 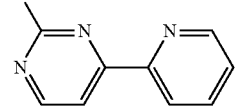 | 29 | 43 |
| 10 | 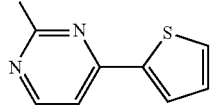 | 21 | 8 |
| 11 | 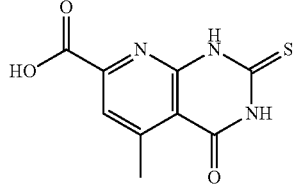 [SMILES: Cc1cc(C(=O)O)nc2[nH]c(=S)[nH]c(=O)c12] | 20 | 50 |
| 12 | 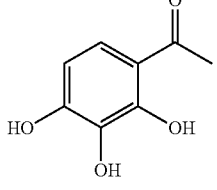 | 22 | 18 |
| 13 | 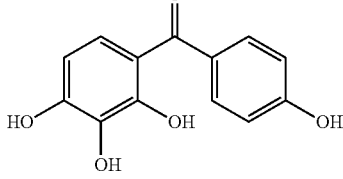 | 48 | 36 |
| 14 | 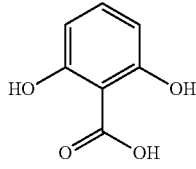 [SMILES: O=C(O)c1c(O)cccc1O] | 4 | 51 |

TABLE 1-continued

| Compound | Compound | VIM-2 | NDM-1 |
|---|---|---|---|
| 15 | (structure: phenyl-NH-C(O)-(CH2)5-C(O)-NH-OH) | 18 | — |
| 16 | (structure: 5-chloro-1H-1,2,4-triazole-3-carboxylic acid hydroxyamide) | 8 | 49 |
| 17 | (structure: 2-phenyl-3-hydroxy-thiazolidin-4-one) | 33 | 40 |
| 18 | (structure: N-hydroxyphthalimide) | 18 | 30 |
| 19 | (structure: 3-hydroxy-2-methylquinazolin-4(3H)-one) | 22 | 46 |
| 20 | (structure: 2-(3,5-dimethyl-1H-pyrazol-1-yl)-3-hydroxyquinazolin-4(3H)-one) | 16 | 81 |
| 21 | (structure: 3-hydroxy-2-thioxo-2,3-dihydroquinazolin-4(1H)-one) | 27 | 78 |
| 22 | (structure: 1-hydroxy-3-(furan-2-yl)quinoxalin-2(1H)-one 4-oxide) | 9 | 12 |

TABLE 1-continued

| | 50 uM single dose percentage inhibition assay | | |
|---|---|---|---|
| Compound | Compound | VIM-2 | NDM-1 |
| 23 | 1-hydroxy-3-(thiophen-2-yl)quinoxalin-2(1H)-one 4-oxide | 25 | 51 |
| 24 | pyridine-2,6-dicarboxylic acid | 15 | 67 |
| 25 | 4-hydroxypyridine-2,6-dicarboxylic acid | 27 | 87 |
| 26 | 2-hydroxy-6-isobutylpyrimidine-4-carboxylic acid | 5 | 58 |
| 27 | 2-hydroxy-6-methylpyrimidine-4-carboxylic acid | 17 | 54 |
| 28 | 2-(hydroxymethyl)-6-methylpyridin-3-ol | 25 | 53 |
| 29 | 4-isopropyl-3-oxo-2,3-dihydro-1H-pyrazolo[3,4-b]pyridine-6-carboxylic acid | 18 | 75 |
| 30 | 4-methyl-3-oxo-2,3-dihydro-1H-pyrazolo[3,4-b]pyridine-6-carboxylic acid | 21 | 66 |

TABLE 1-continued

50 uM single dose percentage inhibition assay

| Compound | Compound | VIM-2 | NDM-1 |
|---|---|---|---|
| 31 | 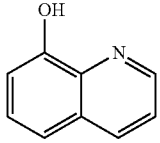 | 98 | 96 |

Each MBL was incubated with 50 µM of each compound, followed by the addition of nitrocefin. The relative change in absorbance is reported as percentage inhibition.

Quinoline is a well-established privilege scaffold in drug discovery (M. E. Welsch, et al., Privileged scaffolds for library design and drug discovery, Curr Opin Chem Biol, 14 (2010) 347-361) with clioquinoline and hydroxyquinoline as prime examples containing the 8HQ moiety. Given its long history in drug discovery, vast numbers of hydroxyquinoline analogues are commercially available for SAR by catalogue study. 8-Hydroxyquinoline (8HQ) has been described as a non-specific monoprotic bidentate chelating agent with antiseptic, disinfectant, pesticide and antiproliferative properties (Oliveri, V.; et al., 8-Hydroxyquinolines in medicinal chemistry: A structural perspective. European Journal of Medicinal Chemistry 2016, 120, 252-274). Although it was recently pursued as a potential agent for treating multi-drug resistant bacterial infections (WO2009140215), there was little or no literature available which systematically establish and characterize the structure activity relationship of 8HQ as a potent MBLi. Furthermore, there is only one available x-ray crystallographic structure of *Aeromonas proteolytica* aminopeptidase that describes the binding mode of 8HQ to a dinuclear zinc enzyme (PDB: 3VH9). Given the current lack of knowledge and the urgency in identifying a novel scaffold for MBLi development, a hit-based substructure search of commercial databases was used to identified 20 additional 8-hydroxyquinoline analogues to establish the preliminary structural activity of this privilege scaffold (Table 2). The compounds were selected to explore the importance of hydroxyl and carboxylic substitutions around the quinolone, and other substitutions around 8-hydroxylquinoline.

TABLE 2

Structure-Activity Relationship of 8-hydroxyquinoline from single-dose percentage inhibition assay

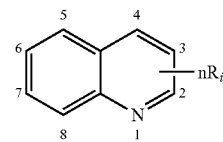

| Compound | n | R1 | R2 | R3 | R4 | VIM-2 | NDM-1 |
|---|---|---|---|---|---|---|---|
| 31 | 1 | 8—OH | | | | 98 | 96 |
| 32 | 1 | 2—OH | | | | 9 | 0 |
| 33 | 1 | 3—OH | | | | 95 | 33 |
| 34 | 1 | 4—OH | | | | 9 | 1 |
| 35 | 1 | 5—OH | | | | 6 | 6 |
| 36 | 1 | 6—OH | | | | 7 | 1 |
| 37 | 1 | 7—OH | | | | 3 | 8 |
| 38 | 1 | 8—NH2 | | | | 43 | 3 |
| 39 | 2 | 8—OH | 1—OH | | | 27 | 7 |
| 40 | 2 | 8—OH | 2—CH3 | | | 77 | 9 |
| 41 | 2 | 8—OH | 5—NO2 | | | 86 | 89 |
| 42 | 2 | 8—OH | 5—NH2 | | | 96 | 86 |
| 43 | 2 | 8—OH | 3—COOH | | | 91 | 90 |
| 44 | 2 | 8—OH | 4—COOH | | | 92 | 88 |
| 45 | 2 | 8—OH | 7—COOH | | | 94 | 99 |
| 46 | 2 | 8—OH | 5—Cl | | | 98 | 94 |
| 47 | 3 | 8—OH | 5—Cl | 7—Cl | | 96 | 90 |
| 48 | 3 | 8—OH | 5—Cl | 7—I | | 93 | 89 |
| 49 | 3 | 8—OH | 5—Br | 7—Br | | 92 | 93 |
| 50 | 4 | 8—OH | 5—Cl | 7—Cl | 2—CH3 | 95 | 93 | where $nR_i$ represent the number, n, of substitutions, R, at each of the designated position, i, around quinoline.

With the exception of compounds 31 and 33, placement of the hydroxyl group at any other position exhibit little or no inhibition against either MBLs. While the bidentating geometry of 8-hydroxyquinoline can be easily rationalized for its potent MBL inhibitory activity, the observed 95% inhibition of 3-hydroxyquinoline against VIM-2 remains unclear and is likely due to an alternative mechanism of inhibition unrelated to zinc binding. Similar to relocating the 8-hydroxyl group, the replacement of a hydroxyl group with an amine at the 8-position, 38, and the addition of a hydroxyl group to the chelating nitrogen atom, 39, obliterate the bidentating geometry of 8-hydroxyquinoline that results in a significant loss of inhibition. Addition of other hydrophilic substituents at 5- and 7-position while maintaining the hydroxyl group at the 8-position is well-tolerated for maintaining potent inhibition. Introduction of an electron donating methyl group at the 2nd position, leads to loss of inhibition on 8-hydroxyquinline, 40, but not in the presence of other halogen substitution at the 5-, and 7-positions, 48. The inhibition activities for the compounds 43-45 with the carboxylic group at the 3- 4- and 7-position respectively were similar among each other with only a slight decrease as compared to the parent 8HQ, 31. Overall, this early SAR study established the placement of hydroxyl group at the 8-position is essential for the potent inhibition of both VIM-2 and NDM-1.

Figure 1B:
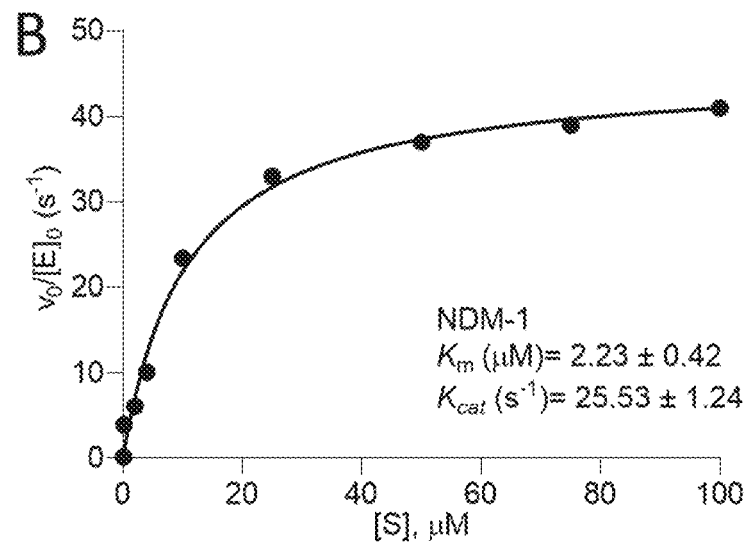
FIG. 1B illustrates the Steady-state kinetics for the hydrolysis of nitrocefin by NDM-1.

In order to establish the inhibition potency of these fragment compounds and its ligand efficiency (LE), the $K_i$ and the $IC_{50}$ for compounds 5, 13, 17, 31 and 41-50 were determined (Table 3). As control for the subsequent study, 1-hydroxypyridine-2 (1H)-thione-6-carboxylic acid, 51 has been included, which has been reported earlier as the first-in-class low cytotoxic MBLi against VIM2 (Shin, W. S., et al., Discovery of 1-hydroxypyridine-2 (1H)-thiones-6-carboxylic acid as a low-cytotoxic, nanomolar metallo b-lactamase inhibitor. ChemMedChem 2017, 12, 845-849.). FIG. 1 shows the steady-state kinetics for the hydrolysis of nitrocefin by NDM-1. The determined $K_m$ and $k_{cat}$ were 2.2 uM and 25 $s^{-1}$ respectively, which are comparable to previously published values (Makena, A.; et al., Biochemical characterization of New Delhi metallo-beta-lactamase variants reveals differences in protein stability. J Antimicrob Chemother 2015, 70, 463-9). The $K_m$ and $k_{cat}$ for VIM-2 were 23.0 uM and 212 $s^{-1}$ and were reported previously (W. S. Shin, et al., Discovery of 1-hydroxypyridine-2 (1H)-thiones-6-carboxylic acid as a low-cytotoxic, nanomolar metallo β-lactamase inhibitor (Shin, W. S.; et al., Discovery of 1-hydroxypyridine-2 (1H)-thiones-6-carboxylic acid as a low-cytotoxic, nanomolar metallo b-lactamase inhibitor. Under Revision). As expected from the modest percentage inhibition, as shown in Table 1, compounds 5, 13, and 17 were expected to exhibit mid-micromolar range of $IC_{50}$ against VIM-2 and NDM-1 with an estimated LE range between 0.39 and 0.61. For the 8-hydroxyquinolines, compounds 31 and 41-50 exhibited low to sub-micromolar inhibition $K_i$ and $IC_{50}$. The most potent compound was 45 with $K_i$'s of 280 nM against VIM-2 and 350 nM against NDM-1 respectively. Given the overall flatness of the SAR for the hydroxyquinolines with or without substitution at the 2-, 5-, and 7-positions, the origin of the observed inhibition is due primarily to the 8-hydroxyquinoline scaffold which, not surprisingly possess the highest LE of 0.77 against VIM-2 and 0.81 against NDM-1 respectively among all 8HQ analogs. Electron-withdrawing halogen substitution at the 2, 5, and 7 positions, 46-50, did not appear to have a significant effect on overall $K_i$ or $IC_{50}$ values.

TABLE 3

Inhibitory activities MBL's

| Compound | N | VIM-2 $K_i$ (μM) | IC50 (μM) | LE | NDM-1 $K_i$ (μM) | IC50 (μM) | LE |
|---|---|---|---|---|---|---|---|
| 5 | 12 | 4.5 | 24 | 0.61 | 7.3 | 68 | 0.59 |
| 13 | 18 | 8.8 | 81 | 0.39 | 7.1 | 68 | 0.39 |
| 17 | 13 | 5.3 | 41 | 0.56 | 5.8 | 52 | 0.56 |
| 31 | 11 | 0.67 | 3.6 | 0.77 | 0.36 | 2.3 | 0.81 |
| 41 | 14 | 0.25 | 0.67 | 0.65 | 0.58 | 1.0 | 0.61 |
| 42 | 12 | 0.88 | 3.8 | 0.70 | 0.99 | 1.7 | 0.69 |
| 43 | 14 | 0.53 | 1.6 | 0.62 | 0.49 | 1.9 | 0.62 |
| 44 | 14 | 0.67 | 2.2 | 0.61 | 0.66 | 1.9 | 0.61 |
| 45 | 14 | 0.28 | 0.74 | 0.65 | 0.35 | 0.76 | 0.64 |
| 46 | 12 | 0.96 | 4.1 | 0.69 | 1.4 | 5.3 | 0.67 |
| 47 | 13 | 1.1 | 4.1 | 0.63 | 1.3 | 6.4 | 0.62 |
| 48 | 13 | 1.1 | 5.1 | 0.63 | 1.2 | 4.8 | 0.63 |
| 49 | 13 | 0.92 | 3.2 | 0.64 | 0.90 | 3.8 | 0.64 |
| 50 | 14 | 0.96 | 4.8 | 0.59 | 1.1 | 5.3 | 0.59 |
| 51 | 11 | 0.02 | 0.31 | 0.97 | 0.42 | 0.81 | 0.80 |

Ligand efficiency (LE) = −1.38 log ($K_i$)/N where N = number of heavy atoms (I. D. Kuntz, et al., The maximal affinity of ligands, P Natl Acad Sci USA, 96 (1999) 9997-10002)

Numerous structural studies have been carried out to examine the exact mechanism of ligand binding for various β-lactam substrates with well-established MBLi's (J. Brem, et al., Structural Basis of Metallo-beta-Lactamase Inhibition by Captopril Stereoisomers, Antimicrob Agents Chemother, 60 (2016) 142-150; M. Aitha, et al., Biochemical, Mechanistic, and Spectroscopic Characterization of Metallo-beta-lactamase VIM-2, Biochemistry-Us, 53 (2014) 7321-7331). For the hydrolyzed meropenem, the mode of binding involved is the oxygen atom of this newly formed carboxylate acting as a bridge chelate between the two dinuclear zinc ions (Zn1 and Zn2) within NDM-1. This results in the formation of a tetracoordinated Zn1 with H120, H122 and H189. The nitrogen of the secondary amine group completes the pentacoordination to the Zn2 ion with D124, H250, and C208. For D-captopril, the binding involved is the formation of the thiolate ion which act as a bridging chelating atom between the two zinc cofactors.

Figure 2A:
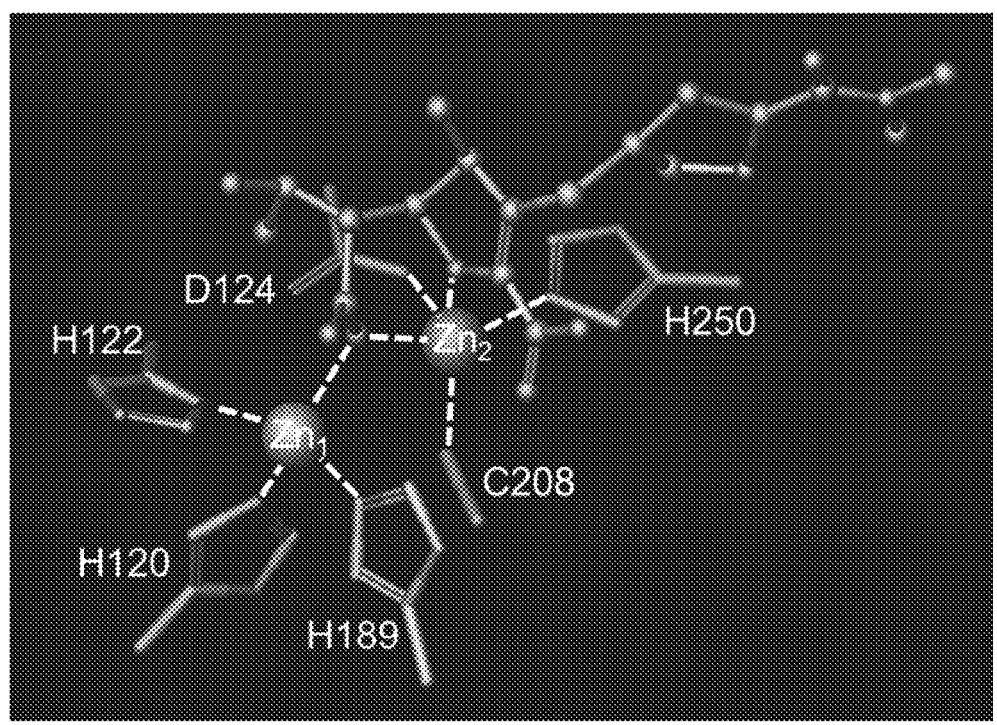
FIG. 2A illustrates the NDM-1 active site with bound hydrolyzed meropenem (top structure in figure) (PDB: 4EYL).
Figure 2B:
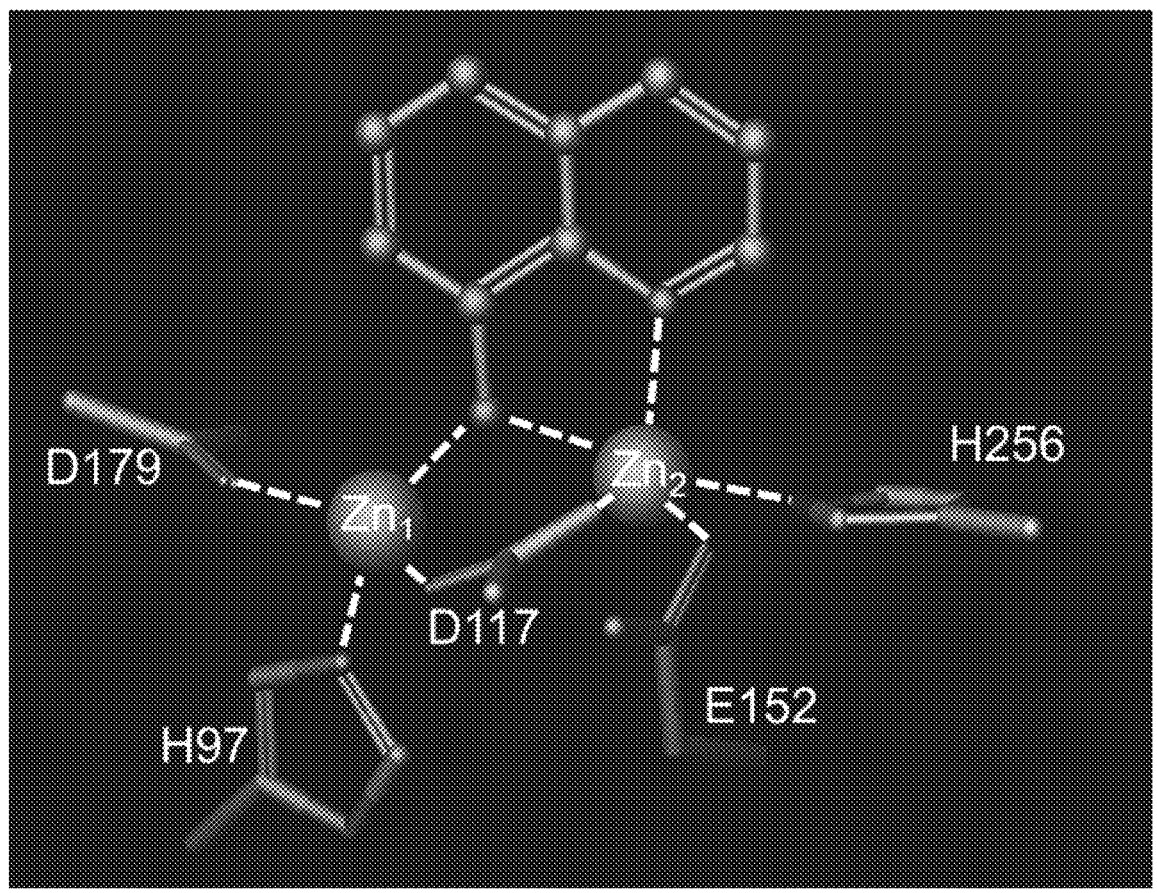
FIG. 2B illustrates the *Aeromonas proteolytica* aminopeptidase active site with bound 8-hydroxyquinoline (top structure in figure) (PDB: 3VH9).

For 8HQ and any of its analogues, there are no X-ray crystallographic structure studies available that shed light onto the potential mechanism of inhibition against any of MBLs. Aeromonas proteolytica aminopeptidase is the only available structure that described the mechanism of binding between 8HQ to a dinuclear $Zn^{2+}$ hydrolase (FIG. 2B) (K. Hanaya, et al., Potent inhibition of dinuclear zinc (II) peptidase, an aminopeptidase from Aeromonas proteolytica, by 8-quinolinol derivatives: inhibitor design based on Zn2+ fluorophores, kinetic, and X-ray crystallographic study, J Biol Inorg Chem, 17 (2012) 517-529). The observed mode of binding was consistent with the observed $pK_a$ of 8HQ, 9.89 and 5.13 for hydroxyl group and nitrogen atom, respectively (A. Albert, J. N. Phillips, 264. Ionization constants of heterocyclic substances. Part II. Hydroxy-derivatives of nitrogenous six-membered ring-compounds, Journal of the Chemical Society (Resumed), (1956) 1294-1304). To improve our understanding of potential mode of binding for 31, molecular modeling was carried out using Schrodinger modeling suites (N.Y. Schrodinger LLC, NY, Maestro v9.7, Bioluminate v1.2, Canvas v1.9, Epik v2.7, Glide v6.2, LigPrep v2.9, MacromModel v10.3, Prime v3.5, Schrodinger LLC, New York, NY, in, 2014). In the presence of the dinuclear zinc, the hydroxyl group is expected to undergo similar deprotonation to form the bridging chelate while the nitrogen atom remain deprotonated to form the pentacoordinated $Zn^{2+}$ (FIG. 3). The carboxylic acid does not appear to impart any improvement in binding affinity as compared to the parent 8HQ, 31.

Figure 4A:
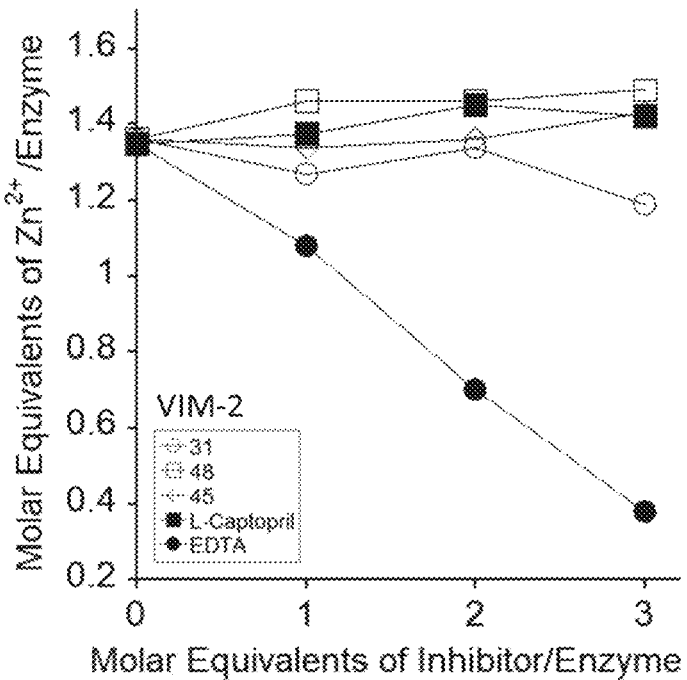
FIGS. 4A and 4B illustrate the equivalents of Zn(II) in FIG. 4A VIM-2 and FIG. 4B NDM-1 samples after incubation with inhibitors and dialysis.
Figure 4B:
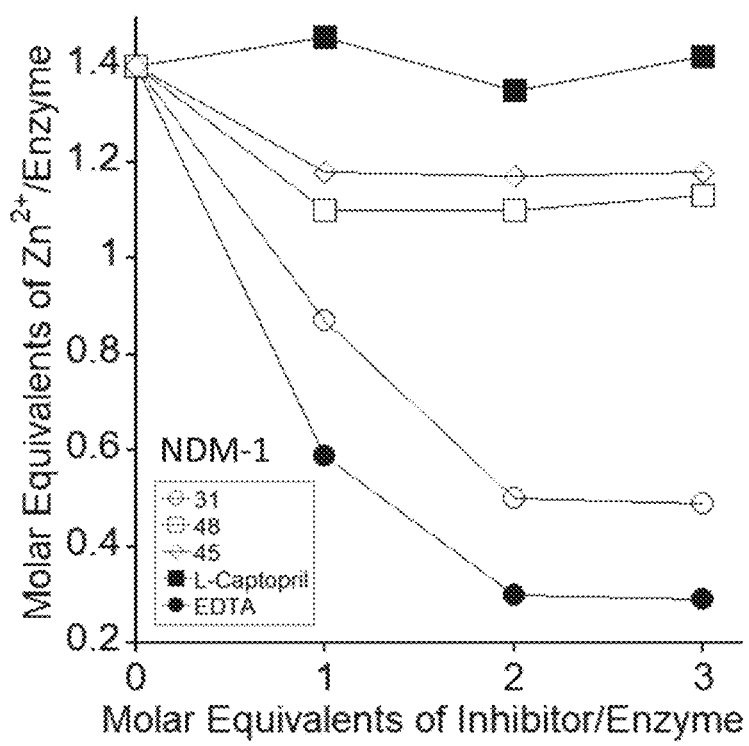
Figure 5A:
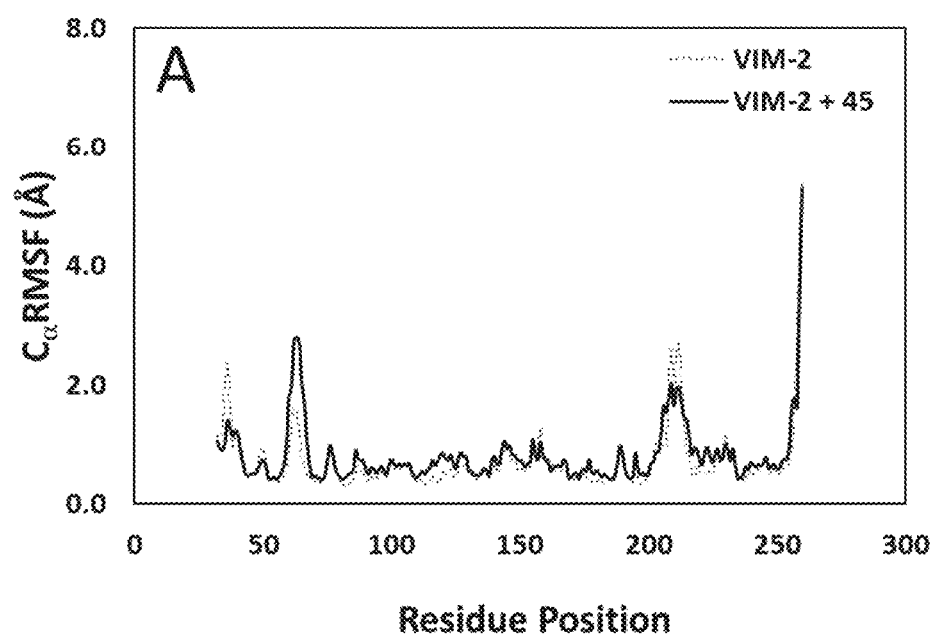
FIGS. 5A and 5B illustrate the $C_\alpha$RMSF analysis of FIG. 4A VIM-2 and FIG. 4B NDM-1 with 45.
Figure 5B:
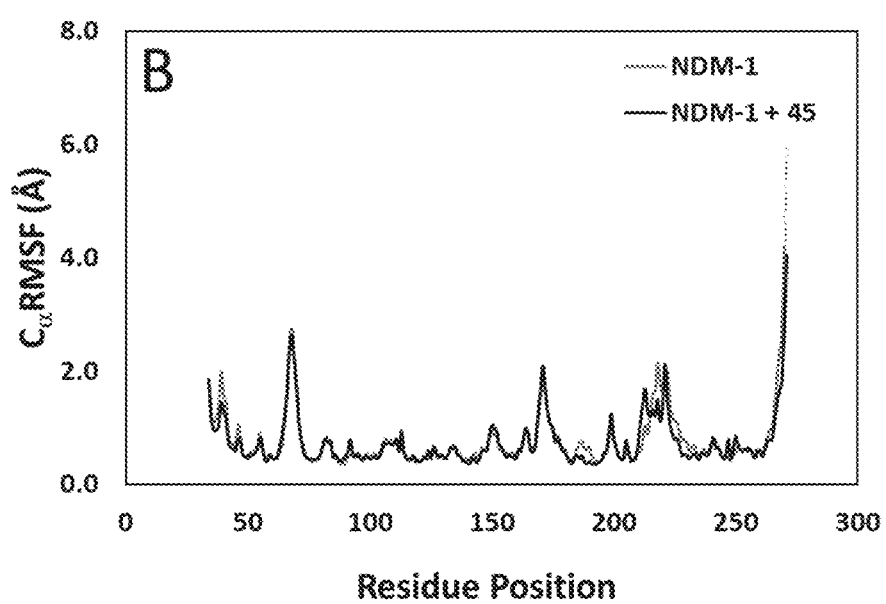

To further address the mode of action of 8-hydroxyquinolines, equilibrium dialysis experiments were conducted. Since parent compound 31 is known to coordinate metal ions, it was not clear whether the mode of inhibition was removal of the Zn(II) or binding to the enzyme-coordinated Zn(II). Therefore, VIM-2 was incubated with increasing concentrations of compounds 31, 45, and 48 (FIG. 4) and equilibrium dialysis and metal analysis was used to evaluate the metal content in the resulting enzyme samples. L-Captopril and EDTA were used as controls because of their contrasting modes of inhibition. EDTA, a well-known metal scavenger, inhibits all MBLs through a chelation mechanism (Bush, K.; Jacoby, G. A. Updated Functional Classification of beta-Lactamases. Antimicrobial Agents and Chemotherapy 2010, 54, 969-976). Equilibrium dialysis studies show that 31, 45 and 48 molar equivalents of EDTA removes 1 equivalent of Zn(II) from VIM-2, under the conditions used in this experiment (FIG. 5). Conversely, L-captopril has been shown to be a competitive inhibitor of several MBLs (Heinz, U.; et al., Coordination geometries of metal ions in d- or l-captopril-inhibited metallo-beta-lactamases. J Biol Chem 2003, 278, 20659-66). In alignment with previous results, the metal content of VIM-2 is relatively unaffected by increasing concentrations of L-captopril. Compounds 31, 45 and 48, like captopril, do not inhibit VIM-2 by removal of Zn(II) from the active site (FIG. 4).

To further demonstrate the ability of 8-hydroxyquinoline in restoring β-lactam antibiotic efficacy, compounds 31, 41, 45 and 48 were evaluated against VIM-2 expressing *E. coli*. Clavulanate was included as control. As shown in Table 4, the growth of wild type *E. coli* can be effectively inhibited by 50 μM of amoxicillin regardless of the presence of the MBLi. The expression of VIM-2 leads to amoxicillin resistance in *E. coli*, rendering the treatment with amoxicillin alone and the amoxicillin-clavulanic acid combination therapy ineffective. Compound 31, which possesses a $K_i$ of 670 nM against VIM2, exhibit potent antibacterial activity against both *E. coli* strains with over 42% growth inhibition on its own, suggesting off-target inhibition and making it unsuitable as a selective inhibitor against β-lactamase for combination antibacterial therapy. Both compounds 45 and 48 exhibit only moderate antibacterial activity on their own against both wild type and VIM-2 expressing *E coli*. As nanomolar inhibitors, both compounds effectively restores amoxicillin efficacy with over 96% synergistic growth inhibition against VIM-2 expressing *E. coli*.

TABLE 4

Single dose cell viability assay (what are the units)

| | E. coli | | VIM-2 expressing E. coli | |
|---|---|---|---|---|
| Compound | Amox (−) | Amox (+) | Amox (−) | Amox (+) |
| Amox | — | 3.6 | — | 77 |
| Clav | 86 | 2.9 | 93 | 57 |
| 31 | 58 | 4.7 | 51 | 5.0 |
| 41 | 65 | 3.6 | 62 | 7.5 |
| 45 | 89 | 4.7 | 79 | 2.8 |
| 48 | 82 | 4.1 | 84 | 3.9 |
| 51 | 82 | 4.1 | 71 | 4.3 |

The data are reported as relative percentage growth compared to untreated cells.

To evaluate the therapeutic index (TI) for compounds 31, 41, 45 and 48, their cytotoxicity against human embryonic kidney HEK 293 cells by MTT assay we assessed as described earlier (R. Muthyala, et al., Cell permeable vanX inhibitors as vancomycin re-sensitizing agents, Bioorg Med Chem Lett, 24 (2014) 2535-2538) and evaluated the effective concentration at which a fixed concentration of antibiotic regains 50% of its growth inhibitory activities ($EC_{50}^*$) (Table 5). The latter approach does not circumvent the need to determine the optimal combination index necessary for future formulation studies, but allow the direct comparison between two potential candidate compounds. As the growth of the wild type *E. coli* can be effectively inhibited at over 96% by amoxicillin alone at 50 uM, the $EC_{50}^*$ for compounds 31, 41, 45 and 48 was determined under the same condition against VIM-2 expressing *E. coli*. The determined $EC_{50}^*$ for compounds 31 and 41 were 80 and 70 nM and were 5 to 10-fold more potent than that of compounds 45 and 48. Of the four compounds evaluated, compound 45 exhibited surprisingly low cytotoxicity with greater than 100 μM $CC_{50}$ against HEK293 cells, that corresponds to a TI of greater 260. This makes compound 45 more than six times better than its parent compound, (31) and thirteen times better than compound 48, an approved topical antifungal drug (Waugh, C. D. Iodochlorhydroxyquin. In xPharm: The Comprehensive Pharmacology Reference, Elsevier: New York, 2007; pp 1-4).

TABLE 5

Cytotoxicity and cell viability assays

| Compound | $CC_{50}$ (μM) | $EC_{50}^*$ (μM) | TI |
|---|---|---|---|
| 31 | 3.5 | 0.08 | 44 |
| 41 | 7.8 | 0.07 | 111 |
| 45 | >100 | 0.38 | >260 |
| 48 | 18.3 | 0.94 | 19 |
| 51 | 92 | 0.21 | 438 |

*$EC_{50}$ was determined in the presence of 50 μM amoxicillin.
Therapeutic index (TI) = $CC_{50}/IC_{50}$.

Finally, to further assess the therapeutic potential of 8-quinonlinol-7-carboxylic acid, 45, its stability in human plasma and human microsomes were also assessed. The half-life's of 45 were determined to be greater than 60 mins in human microsomes and greater than 24 hrs in human plasma, respectively (Table 6), indicating 45 already possesses optimal pharmacokinetic properties for advancing to pre-clinical animal studies.

TABLE 6

Pharmacokinetic studies

| Compound | Human Plasma $t_{1/2}$ (hrs) | Microsomal Stability $t_{1/2}$ (mins) |
|---|---|---|
| 45 | >24 | >60 |

$t_{1/2}$ - Half-life.

As described herein 8-hydroxyquinoline, 31, was identified as a nanomolar inhibitor of VIM-2 and NDM-1. Subsequent hit-based substructure search identified a series of compounds that demonstrate the origin of its potency as a result of the bidenting chemotype for the dinuclear zinc enzymes. Furthermore, given the observed flat SAR, the dominant force governing the inhibition for the series consisting primarily of halogens at the 2-, 5- and 7-position of 8HQ was the metal chelating scaffold with a conserve Ki range of 0.2 to 1.4 uM for both MBLs. Molecular modeling further shed light into its potential mode of binding within the dinuclear zinc binding site. Of four compounds, 31, 41, 45 and 48 (Clioquinol) evaluated, all were able to completely restore the inhibition activity of amoxicillin at 50 μM with a mid to high nanomolar EC50 against VIM-2 expressing *E coli*. Due to their therapeutic risk as a non-specific metal chelator, the CC50 for the four compounds were also determined. 8-Quinolinol-7-carboxylic acid was identified as low cytotoxic broad spectrum nanomolar MBLi against VIM-2 and NDM-1 and was pharmacokinetically stable in human plasma and liver microsomal studies.

Example 2

The following illustrate representative pharmaceutical dosage forms, containing 8-hydroxyquinoline-7-carboxylic acid or a pharmaceutically acceptable salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |

| (i) Tablet 1 | mg/tablet |
|---|---|
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating or preventing a bacterial infection in an animal comprising administering to the animal (a) 8-hydroxyquinoline-7-carboxylic acid or a pharmaceutically acceptable salt thereof, and (b) Amoxicillin, wherein the 8-hydroxyquinoline-7-carboxylic acid is administered orally, and wherein the bacterial infection is caused by *Enterococcus faecium, Staphylococcus aureus, Klebsiella pneumoniae, Acinetobacter baumannii, Pseudomonas aeruginosa, Enterobacter species, Escherichia coli, Neisseria Gonorrhoeae, Campylobacter, Clostridium difficile, Salmonella, Salmonella* serotype *Typhi, Shigella, Streptococcus pneumoniae*, or *Mycobacterium tuberculosis*.

* * * * *